United States Patent [19]

Haas et al.

[11] 4,288,450
[45] Sep. 8, 1981

[54] PROCESS FOR THE PREPARATION OF NOVEL BENZOPYRANE DERIVATIVES

[75] Inventors: Georges Haas, Binningen; Alberto Rossi, Oberwil; Knut A. Jaeggi, Basel; Alex Sele, Muttenz, all of Switzerland

[73] Assignee: Ciba-Geigy Corporation, Ardsley, N.Y.

[21] Appl. No.: 110,077

[22] Filed: Jan. 7, 1980

Related U.S. Application Data

[62] Division of Ser. No. 923,522, Jul. 11, 1978, Pat. No. 4,216,155.

[30] Foreign Application Priority Data

Jul. 15, 1977 [LU] Luxembourg ............................ 77786

[51] Int. Cl.³ .................... C07D 311/22; A61K 31/35
[52] U.S. Cl. .................................. 424/283; 260/345.2
[58] Field of Search .......... 260/345.2, 340.3, 340.5 R; 424/283

[56] References Cited

U.S. PATENT DOCUMENTS 3,862,143  1/1975  Klutchko et al. ............... 260/345.2
3,937,719  2/1976  Sellstedt et al. ................ 260/345.2
3,952,013  4/1976  Hazard et al. .................. 260/345.2
4,076,729  2/1978  Connor et al. .................. 260/345.2

*Primary Examiner*—Nicky Chan
*Attorney, Agent, or Firm*—Prabodh I. Almaula

[57] ABSTRACT

The present invention relates to novel benzopyrane derivatives, especially 3-oxaloamino-4-oxo-4H-1-benzopyrane derivatives of the formula I

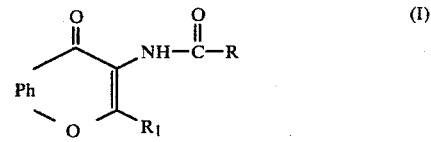

in which Ph is substituted or unsubstituted 1,2-phenylene, R is free, esterified or amidated carboxyl and $R_1$ is hydrogen or a substituted or substituted hydrocarbon radical, in the free from or in the form of a salt, exhibit antiallergic activities and are accordingly useful as active ingredients of antiallergic pharmaceutical preparations.

8 Claims, No Drawings

PROCESS FOR THE PREPARATION OF NOVEL BENZOPYRANE DERIVATIVES

This is a divisional of application Ser. No. 923,522 filed on July 11, 1978, now U.S. Pat. No. 4,216,155.

The present invention relates to novel benzopyrane derivatives, especially 3-oxaloamino-4-oxo-4H-1-benzopyrane derivatives of the formula I

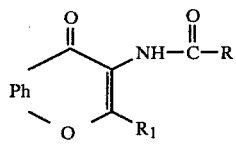

in which Ph is substituted or unsubstituted 1,2-phenylene, R is free, esterified or amidated carboxyl and $R_1$ is hydrogen or a substituted or unsubstituted hydrocarbon radical, with the proviso that Ph is substituted 1,2-phenylene different from 1,2-phenylene monosubstituted by halogen, hydroxy, lower alkoxy or lower alkyl, when $R_1$ denotes hydrogen or lower alkyl and R denotes carboxy or carboxy esterified with a lower alkanol, in the free form or in the form of a salt, processes for the preparation thereof, pharmaceutical preparations containing these derivatives and the use of compounds of the formula I as a pharmaceutical or for the production of pharmaceutical preparations.

Substituted or unsubstituted 1,2-phenylene can be mono- or poly-substituted and substituents are, for example, aliphatic radicals, such as lower alkyl or lower alkylene bonded to two adjacent C atoms, acyl radicals, such as lower alkanoyl, free, etherified or esterified hydroxyl, such as lower alkoxy, hydroxy-lower alkoxy or lower alkylenedioxy bonded to two adjacent C atoms, or halogen, and trifluoromethyl.

Free, esterified or amidated carboxyl is, for example, carboxyl esterified by an alcohol of aliphatic character, carbamyl which is unsubstituted or substituted by at least one substituted or unsubstituted aryl or hydrocarbon radical of aliphatic character, or a heteroanalogue thereof, hydroxyl or primary amino, or, in particular, free carboxyl.

An alcohol of aliphatic character is an alcohol in which the C atom bonded to the hydroxyl group is not a member of an aromatic system, for example a lower alkanol which is unsubstituted or substituted by a substituted or unsubstituted phenyl, or a cycloaliphatic alcohol, for example a 5-membered to 8-membered cycloalkanol. Examples of carboxyl esterified by a substituted or unsubstituted alcohol of aliphatic character are: lower alkoxycarbonyl, for example methoxycarbonyl, ethoxycarbonyl, propoxycarbonyl, isopropoxycarbonyl and butoxycarbonyl, phenyl-lower alkoxycarbonyl, in particular α- and β-phenyl-lower alkoxycarbonyl, which can be substituted in the phenyl moiety, for example substituted or unsubstituted benzyloxycarbonyl and α- and β-phenethoxycarbonyl, and 5-membered to 8-membered cycloalkoxycarbonyl, for example cyclopentyloxycarbonyl, cyclohexyloxycarbonyl and cycloheptyloxycarbonyl.

In a substituted or unsubstituted hydrocarbon radical of aliphatic character, or a hetero-analogue thereof, which is a substituent or a carbamyl group, the free valency emanates from a non-aromatic c atom. Such a radical is, for example, lower alkyl or lower alkenyl, which can be substituted, for example, by substituted or unsubstituted phenyl, or, for example, 5-membered to 8-membered cycloalkyl, such as cyclohexyl, or unsubstituted or lower alkylated 4-membered to 7-membered alkylene, or a mono-oxa, -aza- or -thia-analogue thereof, for example tetra- or penta-methylene or 3-oxa-, 3-aza- or 3-thia-pentamethylene. Examples of carbamyl substituted by at least one such radical are: mono- or di-lower alkyl-carbamyl, for example N-methyl-, N-ethyl- or N,N-diethyl-carbamyl, phenyl-lower alkylcarbamyl which can be substituted in the phenyl moiety, such as N-benzyl- or N-(1- or 2-phenethyl)-carbamyl, or pyrrolidinocarbonyl, piperidinocarbonyl, morpholinocarbonyl, thiomorpholinocarbonyl, piperazinocarbonyl or 4-lower alkylpiperazinocarbonyl, for example 4-methylpiperazinocarbonyl.

A substituted or unsubstituted hydrocarbon radical $R_1$ is, for example, a substituted or unsubstituted hydrocarbon radical of aliphatic character or a substituted or unsubstituted aromatic hydrocarbon radical.

In a substituted or unsubstituted hydrocarbon radical of aliphatic character the free valency emanates from a non-aromatic C atom. A radical of this type is, for example, an aliphatic, hydrocarbon radical, for example a lower alkyl radical, which is unsubstituted or, less preferentially, substituted by substituted or unsubstituted phenyl, or, furthermore, is a cycloaliphatic hydrocarbon radical, such as 5-membered to 8-membered cycloalkyl or cycloalkenyl, for example 1-cycloalkenyl. Particular examples of such radicals are: methyl, ethyl, isopropyl and butyl and also benzyl, cyclopentyl, cyclohexyl and cycloheptyl.

A substituted or unsubstituted aromatic hydrocarbon aryl radical is, for example, substituted or unsubstituted phenyl.

In this specification organic compounds or radicals qualified by the term "lower" have not more than 7 and in particular not more than 4 C atoms and can be straight-chain or branched.

Substituted or unsubstituted phenyl and also phenyl in substituted or unsubstituted phenyl-lower alkyl and phenyl-lower alkoxy is, for example, unsubstituted or mono- or poly-substituted phenyl, substituents being, in particular, lower alkyl, lower alkoxy and halogen, for example those mentioned below, and also trifluoromethyl, such as phenyl, o-, m- or p-tolyl, o-, m- or p-anisyl, o-, m- or p-chlorophenyl or 2,4-, 3,5- or 2,6-dichlorophenyl.

Lower alkyl is, for example, methyl, ethyl, propyl or n-butyl or also isopropyl or sec.-, iso- or tert.-butyl.

Lower alkoxy, including that in lower alkoxycarbonyl, is, for example, methoxy, ethoxy, propoxy, isopropoxy, butoxy or amyloxy.

Lower alkanoyl is, for example, acetyl, propionyl, butyryl, isobutyryl, valeroyl, pivaloyl or caproyl.

Hydroxy-lower alkoxy has not more than 3 hydroxyl groups, which are preferably bonded in positions higher than the α-position, and is in particular 2- or 3-hydroxy-lower alkoxy, for example 2-hydroxyethoxy.

Lower alkylene is, for example, 3-membered to 5-membered, in particular 3-membered or 4-membered, lower alkylene, such as 1,3-propylene, 1,4-butylene or 1,5-pentylene.

Lower alkylenedioxy is, for example, 3-membered to 4-membered lower alkylenedioxy, for example methylene-dioxy, ethylidenedioxy, ethylenedioxy or 1,3-propylene-dioxy.

Halogen is, for example, halogen with an atomic number of not more than 35, such as fluorine, chlorine or bromine.

Salts of compounds of the general formula (I) in which R is carboxyl are salts with bases, in particular corresponding pharmaceutically usable salts, such as alkali metal salts or alkaline earth metal salts, for example sodium salts, potassium salts, magnesium salts or calcium salts, and also ammonium salts with ammonia or amines, such as lower alkylamines or hydroxy-lower alkylamines, for example trimethylamine, triethylamine or di-(2-hydroxyethyl)-amine.

The novel compounds have valuable pharmacological properties. In particular, they have antiallergic actions, as can be shown, for example, on rats in doses as low as 3 mg/kg administered orally or as low as about 0.3 to about 10 mg administered intravenously, in the passive cutaneous anaphylaxis test (PCA reaction). This test is carried out analogously to the method described by Goose and Blair, Immunology, volume 16, page 749 (1969), the passive cutaneous anaphylaxis being produced by the procedure described by Ovary, Progr. Allergy, volume 5, page 459 (1958) or by inhibition of the release of histamine, for example from the peritoneal cells of rats in vitro (cf. Dukor et al., Intern. Arch. Allergy (1976) to be published).

Oxaloamino-4-oxo-4H-1-benzopyrane compounds of pharmacological interest are already known. For example, in U.S. Pat. No. 4,076,279, the subject matter of which is herein disclaimed in toto, 3-Oxaloamino-4-oxo-4H-1-benzopyranes of the general formula I are disclosed. In addition, re U.S. Pat. No. 3,937,719 is referred to.

The compounds of the present invention are accordingly outstandingly useful as inhibitors of allergic reactions, for example in the treatment and prophylaxis of allergic diseases, such as asthma, including both extrinsic and intrinsic asthma, or other allergic diseases, such as hay fever, conjunctivitis, urticaria and enzema.

The invention relates, for example, to compounds of the formula I in which R is carboxyl esterified by a substituted or unsubstituted phenyl-lower alkanol or a cycloaliphatic alcohol or is amidated carboxyl and Ph and $R_1$ are as defined, or in which $R_1$ is an aliphatic hydrocarbon radical substituted by substituted or unsubstituted phenyl, a cycloaliphatic hydrocarbon radical or a substituted or unsubstituted aromatic hydrocarbon radical and R and Ph are as defined, or in which Ph is 1,2-phenylene which is monosubstituted by acyl, hydroxy-lower alkoxy or trifluoromethyl or disubstituted by lower alkyl, lower alkoxy, halogen, hydroxy-lower alkoxy and/or hydroxyl or, on two adjacent C atoms, by lower alkylene or lower alkylenedioxy and R and $R_1$ are as defined, in each case in the free form or in the form of a salt, processes for the preparation thereof, pharmaceutical preparations containing these compounds and their use as pharmaceuticals or for the production of pharmaceutical preparations.

The invention relates particularly to compounds of the general formula I in which R is carboxyl, carboxyl esterified by an alcohol of aliphatic character or carbamyl which is unsubstituted or substituted by at least one substituted or unsubstituted hydrocarbon radical of aliphatic character, or a hetero-analogue thereof, or by hydroxyl or primary amino, Ph is 1,2-phenylene which is unsubstituted or monosubstituted or polysubstituted by aliphatic radicals, acyl radicals, free, etherified or esterified hydroxyl and/or trifluoromethyl and $R_1$ is hydrogen, a substituted or unsubstituted hydrocarbon radical of aliphatic character or a substituted or unsubstituted aromatic hydrocarbon radical, substituents of aromatic groups being, in each case, in particular lower alkyl, lower alkoxy, halogen and trifluoromethyl, in the free form or in the form of a salt.

The invention relates in particular to compounds of the general formula I in which R is carboxyl, carboxyl esterified by a lower alkanol or carbamyl which is unsubstituted, monosubstituted by lower alkyl or, less preferentially, disubstituted by lower alkyl, lower alkylene or 3-oxa-, 3-aza- or 3-thia-lower alkylene, Ph is 1,2-phenylene which is unsubstituted or substituted by lower alkyl, such as methyl, 3-membered or 4-membered lower alkylene, such as 1,3-propylene, hydroxyl, lower alkoxy, such as methoxy, hydroxy-lower alkoxy, in which the hydroxyl group is bonded in a position higher than the α-position, such as 2-hydroxyethoxy, 3-membered or 4-membered lower alkylenedioxy, such as methylenedioxy or ethylenedioxy, lower alkanoyl, such as acetyl or butyryl, trifluoromethyl and/or halogen, such as chlorine, and $R_1$ is hydrogen or, less preferentially, lower alkyl, in the free form or in the form of a salt.

The invention relates especially to compounds of the general formula I in which R is carboxyl or, less preferentially lower alkoxycarbonyl, such as methoxycarbonyl or ethoxycarbonyl, or carbamyl which is unsubstituted or mono- or di-substituted by lower alkyl, such as methyl or ethyl, Ph is 1,2-phenylene which is unsubstituted or substituted by lower alkyl, such as methyl, 3-membered or 4-membered lower alkylene, such as 1,3-propylene, hydroxyl, lower alkoxy, such as methoxy, 2- or 3-hydroxy-lower alkoxy, such as 2-hydroxyethoxy, 3-membered or 4-membered lower alkylenedioxy, such as methylenedioxy or ethylenedioxy, lower alkanoyl, such as acetyl or butyryl, and/or halogen, such as chlorine, and $R_1$ is hydrogen or, less preferentially, lower alkyl, such as methyl, in the free form or in the form of a salt.

The invention relates primarily to compounds of the general formula I in which R is carboxyl or, less preferentially, lower alkoxycarbonyl having not more than 5 C atoms, such as methoxycarbonyl or ethoxycarbonyl, Ph is 1,2-phenylene which is unsubstituted or substituted in one of the free positions by lower alkyl having not more than 4 C atoms, such as methyl, 3-membered or 4-membered lower alkylene having not more than 4 C atoms, such as 1,3-propylene, lower alkoxy having not more than 4 C atoms, such as methoxy, 3-membered or 4-membered lower alkylenedioxy, such as methylenedioxy or ethylenedioxy, lower alkanoyl having not more than 7 C atoms, such as acetyl or butyryl, hydroxyl and/or halogen with an atomic number of not more than 35, such as chlorine, and $R_1$ is hydrogen, lower alkyl having not more than 4 C atoms, such as methyl, or phenyl, in each case in the free form or in the form of a salt.

The invention relates primarily, for example, to compounds of the general formula I in which R is carboxyl, Ph is 1,2-phenylene which is unsubstituted, monosubstituted by lower alkyl having not more than 4 C atoms, such as methyl, lower alkoxy having not more than 4 C atoms, such as methoxy, lower alkanoyl having not more than 7 C atoms, such as butyryl, or halogen with an atomic number of not more than 35, such as chlorine, or disubstituted by lower alkyl having not more than 4 C atoms, such as methyl, lower alkoxy having not more than 4 C atoms, such as methoxy, halogen with an atomic number of not more than 35, such as chlorine, and/or lower alkanoyl having not more than 7 C atoms, such as butyryl, or, on two adjacent C atoms, by 3-membered or 4-membered lower alkylene having not more than 4 C atoms, such as 1,3-propylene, and $R_1$ is hydrogen, in the free form or in the form of a salt.

The invention relates very particularly to compounds of the formula Ia

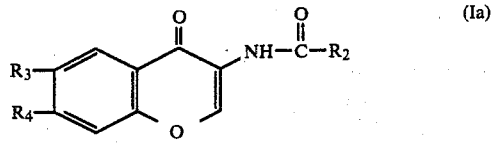

in which $R_2$ is carboxyl and $R_3$ and $R_4$ independently of one another are hydrogen, lower alkyl having not more than 4 C atoms, such as methyl, lower alkoxy having not more than 4 C atoms, such as methoxy, lower alkanoyl having not more than 7, for example not more than 4, C atoms, such as acetyl or butyryl, hydroxyl or halogen with an atomic number of not more than 35, such as chlorine, or together are a lower alkylene or lower alkylene-dioxy radical having not more than 4 C atoms, such as 1,3-propylene, methylenedioxy or ethylenedioxy, in the free form or in the form of a salt.

The invention relates preferentially to compounds of the formula Ia in which $R_2$ is carboxyl and $R_3$ and $R_4$ either are hydrogen or, independently of one another, $C_1$-$C_4$-alkyl, such as methyl, or together are $C_3$- or $C_4$—alkylene, such as 1,3-propylene, in the free form or in the form of a salt.

The invention relates specifically to the compounds of the formula I named in the examples, in the free form or in the form of a salt.

The novel compounds can be prepared by processes known per se.

A preferred procedure comprises, for example, reacting a compound of the general formula II

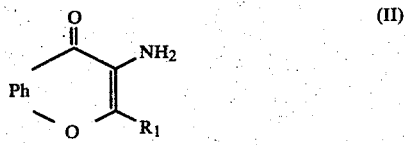

or an acid addition salt thereof, with a compound of the formula R—X (III), in which X is a free or functionally modified carboxyl group, and, if desired, converting a compound thus obtainable into another compound of the formula I and/or converting a resulting salt into the free compound or into another salt, or converting a resulting salt-forming compound into a salt.

Acid addition salts of compounds of the formula II are, for example, hydrohalides, such as hydrochlorides, thereof, and also salts with acids of the formula III.

Functionality modified carboxyl groups X are, for example, esterified or amidated carboxyl groups or carboxyl groups which have been converted to an anhydride, such as lower alkoxycarbonyl, substituted or unsubstituted carbamyl, for example carbamyl, di-lower alkylcarbamyl or imidazolyl-1-carbonyl, or halogenocarbonyl, for example chlorocarbonyl or bromocarbonyl. Examples of starting materials of the formula III are, in particular: oxalic acid, oxalic acid diesters, such as di-lower alkyl oxalates, and free, esterified or amidated halogeno-oxalic acids, such as lower alkyl chloro- or bromo-oxalates or chloro- or bromo-oxalic acid di-lower alkylamides, specifically diethyl oxalate and ethyl bromo- or chloro-oxalate.

The reaction of compounds of the formulae II and III can be carried out in a conventional manner, for example in the presence of a water-binding agent, such as an acid anhydride, for example phosphorus pentoxide, or dicyclohexylcarbodiimide, or of a condensing agent, for example an acid or basic condensing agent, such as a mineral acid, for example hydrochloric acid, or of an alkali metal hydroxide or alkali metal carbonate, for example sodium hydroxide or potassium hydroxide, or of an organic nitrogen base, for example triethylamine or pyridine. When the reaction is carried out with an ester-halide or amide-halide of oxalic acid, the condensing agent used is preferably an organic nitrogen base. The reaction with oxalic acid is preferably carried out in the presence of a water-binding agent or acid condensing agent which effects dehydration of the substituted ammonium salt first formed. If necessary, the reaction is in each case carried out in an inert solvent or diluent, such as a hydrocarbon, for example toluene, a N,N-di-lower alkylamide, for example dimethylformamide, or in chloroform or methylene chloride, at normal temperature or with cooling or warming, for example in the temperature range from about 0° to 100° C., in a closed vessel and/or under an inert gas, for example under nitrogen.

The starting materials of the formula II are known or can be prepared by methods known per se, for example by reducing the nitro group in a corresponding 3-nitro-4-oxo-4H-1-benzopyrane derivative to an amino group in a conventional manner, for example by treatment with hydrogen catalytically activated by palladium-on-active charcoal, for example in the dimethylformamide under normal pressure.

The abovementioned 3-nitro-4-oxo-4H-1-benzopyrane derivatives are in turn known or can be prepared by methods known per se, for example by subjecting a corresponding methylsulphinylacetophenone of the formula HO—Ph—C(=O)—CH$_2$—S(=O)—CH$_3$ to a condensation reaction in the presence of a base, for example of potassium carbonate in water, with an aldehyde of the formula $R_1$—CHO, for example formaldehyde, eliminating sulphinic acid from the 2-$R_1$-3-hydroxymethyl-3-methylsulphinyl-2,3-dihydro-4-oxo-4H-1-benzopyrane derivative thus obtainable, by the action of heat, for example in boiling toluene, and moderately warming the 2-$R_1$-3-hydroxymethyl-4-oxo-4H-benzopyrane derivative thus obtainable, for example to about 40° C., with concentrated, for example 70%, nitric acid. A direct procedure for forming the said nitro compounds comprises heating a corresponding α-nitroacetophenone of the formula HO—Ph—C(=O)—CHR$_1$—NO$_2$ in the presence of sodium formate with the mixed anhydride of acetic acid and formic acid, for example to the boiling point.

The novel compounds can also be prepared by converting $X_1$ in a compound of the formula

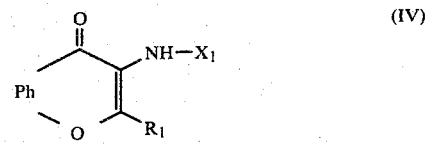

in which $X_1$ is a radical which can be converted to the desired group of the formula R—C(=O)—, into the group of the formula R—C(=O)— and, if desired, converting a compound thus obtainable into another compound of the formula I and/or converting a resulting salt into the free compound or into another salt or converting a resulting salt-forming compound into a salt.

A radical which can be converted to a group of the formula R—C(=O)— is, for example, a functionally modified oxalo group which differs from a free, esterified or amidated oxalo group and can be converted into the latter. Functionally modified oxalo groups of this type are, preferably, those which contain, as a functionally modified α-carbonyl grouping, thioxomethylene, iminomethylene or an esterified and/or etherified dihydroxymethylene grouping and/or which contain, as a functionally modified carboxyl group, a functionally modified carboxyl group which differs from an esterified or amidated carboxyl group. Esterified and/or etherified dihydroxymethylene groupings are, for example, dihydroxymethylene groupings esterified by a hydrogen halide acid, such as hydrochloric acid, and/or etherified by a lower alkanol, such as methanol or ethanol. Examples are, in particular, dihalogenomethylene groupings, such as dichloromethylene, lower alkoxy-halogenomethylene groupings, such as methoxy- or ethoxy-chloromethylene, or di-lower alkoxy-methylene groupings, such as dimethoxy- or diethoxy-methylene. Functionally modified carboxyl groupings which differ from esterified or amidated carboxyl groups are, for example, the cyano group, carboxyl groups in the form of an anhydride, such as halogenocarbonyl, for example chlorocarbonyl, imino-ester-halide groupings, such as imide- or amide-halide groupings, for example iminochloromethyl or aminodichloromethyl, iminoether groupings, such as lower alkyl- or lower alkylene-imino-ether groupings, for example methoxy- or ethoxy-iminomethyl, 4,4- or 5,5-dimethyloxazolin-2-yl or 4,4,6-trimethyl-dihydro-oxazin-2-yl, amidino groups, such as amidino or lower alkyl-amidino, for example methylamidino, ortho-acid groupings esterified by a hydrogen halide acid, such as hydrochloric acid, and/or etherified by a lower alkanol, such as tri-lower alkoxy-methyl, lower alkoxy-dihalogeno-methyl or trihalogeno-methyl groups, in particular trimethoxymethyl or triethoxymethyl, ethoxydichloromethyl or trichloromethyl, or free or esterified thiocarboxyl groups, such as lower alkyl-thiocarbonyl groups, for example ethylthiocarbonyl.

Groups $X_1$ of this type can be converted by solvolysis into a group of the formula R—C(=O)—, for example by hydrolysis into the oxalo group. Groups $X_1$ which contain an imino-ether, ortho-ester or ester-halide grouping as a functionally modified carboxyl group and/or contain thioxomethylene or iminomethylene or an esterified or etherified dihydroxymethylene group as a functionally modified α-carbonyl group can also be hydrolysed to esterified oxalo groups. Likewise, groups $X_1$ which contain the cyano group or an amidino or imide-halide or amide-halide grouping as a functionally modified carboxyl group and/or contain thioxomethylene or iminomethylene or an etherified or esterified dihydroxymethylene group as a functionally modified α-carbonyl group can be hydrolysed to amidated carboxyl groups. The hydrolysis can be carried out in a customary manner, if necessary in the presence of a basic or, preferably, acid hydrolysing agent, such as of an alkali metal hydroxide, such as sodium hydroxide or potassium hydroxide, or preferably of a proton acid, preferably a mineral acid, for example a hydrogen halide acid, such as hydrochloric acid, or of an organic carboxylic acid or sulphonic acid, for example acetic acid or p-toluenesulphonic acid, if necessary in a polar solvent, such as a lower alkanol, ketone or ether, for example in ethanol, acetone or dioxane, and/or with cooling or warming, for example at about 0° C. to about 100° C.

Functionally modified oxalo groups containing, as a functionally modified carboxyl group, a carboxyl group in the form of an anhydride, such as halogenocarbonyl, for example chlorocarbonyl, or a lower alkyleneimino-ether grouping, for example 4,4- or 5,5-dimethyl-oxazolin-2-yl or 4,4,6-trimethyl-dihydrooxazin-2-yl, can also be converted into esterified oxalo groups by conventional alcoholysis, i.e. by reaction with the corresponding alcohol. In the case of alcoholysis of carboxyl groups in the form of an anhydride, the reaction is advantageously carried out in the presence of a basic condensing agent, for example of pyridine or triethylamine, whilst the alcoholysis of a lower alkyleneimino-ether grouping is preferably carried out under acid conditions, for example in the presence of hydrochloric acid, p-toluenesulphonic acid or acetic acid. In an analogous manner, a functionally modified oxalo group containing a carboxyl group in the form of an anhydride can also be converted into an amidated oxalo group R—C(=O)— by ammonolysis or aminolysis, i.e. by reaction with ammonia or a corresponding primary or secondary amine, preferably in the presence of a basic condensing agent, for example of sodium hydroxide, pyridine or triethylamine.

Further radicals $X_1$ which can be converted into groups of the formula R—(=O)— are, for example, groups which can be converted into the said groups by oxidation, especially the glyoxyloyl group which can be converted by oxidation into the oxalo group of the formula R—C(=O)—, in which R is carboxyl, and which may be hydrated. This group can advantageously be formed in situ in the course of the oxidation reaction, for example from the acyl group of an aliphatic or araliphatic carboxylic acid which can be α,β-unsaturated or α,β-dihydroxylated, a glycoloyl group, which can be esterified on the hydroxyl group, or the glycyl group, or can be set free from one of its functional derivatives, for example from one of its acetals or imines. Acyl groups of carboxylic acids which can be α,β-unsaturated or α,β-dihydroxylated are, for example, alkanoyl groups, such as lower alkanoyl, for example acetyl, acyl groups of α,β-unsaturated aliphatic monocarboxylic or dicarboxylic acids, for example acryloyl, crotonyl or the acyl group of free or functionally modified fumaric acid or maleic acid, acyl groups of α,β-unsaturated araliphatic carboxylic acids, for example substituted or unsubstituted cinnamoyl, or acyl groups of aliphatic α,β-dihydroxydicarboxylic acids, such as of tartaric acid, or monofunctional carboxy derivatives, such as esters or amides, thereof. Esterified glycoloyl groups are, for example, glycoloyl groups esterified on the hydroxyl group by a mineral acid, such as a hydrogen halide acid, for example by hydrochloric acid or hydrobromic acid, or by a carboxylic acid, for example by acetic acid or substituted or unsubstituted benzoic acid. Acetalised glyoxyloyl groups are, for example, glyoxyloyl groups acetalised by lower alkanols or a lower alkanediol, such as dimethoxy- diethoxy- or ethylenedioxy-acetyl. Imines of glyoxyloyl groups are, for example, substituted or unsubstituted N-benzylimines thereof. Further radicals which can be converted by oxidation into the oxalo group are, for example, substituted or unsubstituted 2-furoyl groups, such as 2-furoyl groups which contain an acetalised formyl group, such as diethoxymethyl, in the 5-position. Groups which can be oxidised to esterified oxalo groups of the formula R—C(=O)—, in which R is esterified carboxyl, are etherified glycoloyl groups, such as lower alkoxy-acetyl. Radicals which can be oxidised to free, esterified or amidated oxalo groups are, furthermore, free, esterified or amidated carboxymethyl groups.

The oxidation of such groups $X_1$ can be carried out in a customary manner by reaction with a suitable oxidising agent. Suitable oxidising agents are, especially, oxidising heavy metal compounds, such as silver compounds, for example silver nitrate or silver picolinate, oxy-acids of heavy metals, for example of manganese-IV and -VII, lead-IV, chromium-VI or iron-VI, or of halogens, or their anhydrides or salts, such as chromic acid, chromium tridioxide, potassium dichromate, potassium permanganate, manganese dioxide, potassium ferrate, sodium iodate, sodium periodate or lead tetraacetate. The reaction with these oxidising agents is effected in a customary manner, for example in an inert solvent, such as acetone, sulphuric acid, pyridine or water, or a mixture, preferably an aqueous mixture, of inert solvents, at normal temperature or, if necessary, with cooling or warming, for example at about 0° C. to about 100° C. The oxidation of free or etherified glycoloyl groups to free or esterified oxalo groups is, for example, advantageously carried out with potassium permanganate in aqueous pyridine or acetone at room temperature. Acetalised glyoxyloyl groups and iminoacetyl groups are preferably oxidised under acid conditions, for example with potassium dichromate in sulphuric acid. Acyl groups of α,β-dihydroxylated aliphatic carboxylic acids, such as the acyl radical of tartaric acid, are advantageously oxidised with periodic acid, whilst potassium ferrate in an alkaline medium, for example at pH=10 to 13, for example 11.5, or organic silver salts, such as silver picolinate, are preferably used for the oxidation of the glycyl group.

Most of the compounds of the formula IV which have been mentioned as starting materials are novel. In addition to the fact that they can be used as starting materials for the preparation of compounds of the formula I, some of them show further advantageous properties. Thus, compounds of the formula IV in which $X_1$ is a free, esterified or etherified glycoloyl group show the same pharmacological properties, in an activity of comparable strength, as the corresponding compounds of the formula I.

The invention accordingly also relates to novel starting materials, in particular compounds of the formula IV in which $X_1$ is a free, esterified or etherified glycoloyl group, processes for their preparation, pharmaceutical preparations containing these compounds and the use of these preparations as pharmaceuticals or for the preparation of medicaments.

Esterified glycoloyl groups are to be understood as meaning, for example, glycoloyl groups esterified by a carboxylic acid, such as an aliphatic or aromatic carboxylic acid, for example corresponding lower alkanoyloxy-acetyl or substituted or unsubstituted benzoyloxyacetyl. Lower alkanoyloxy-acetyl is, for example, acetoxy-, propionyloxy-, butyryloxy-, isobutyryloxy-, valeroyloxy-, caproyloxy- or pivaloyloxy-acetyl. Substituents of substituted benzoyloxy-acetyl groups are, in particular, lower alkyl, such as methyl, lower alkoxy, such as methoxy, and/or halogen, such as chlorine.

Etherified glycoloyl groups are, for example, glycoloyl groups etherified by a substituted or unsubstituted, aliphatic or araliphatic alcohol, such as corresponding lower alkoxy-acetyl or phenyl-lower alkoxy-acetyl groups. Substituents of lower alkoxy-acetyl are, in particular, hydroxyl, lower alkoxy and/or di-lower alkylamino and substituents of phenyl-lower alkoxy-acetyl groups are, for example, lower alkyl, such as methyl, lower alkoxy, such as methoxy, and/or halogen, such as chlorine. Lower alkoxy preferably has one of the meanings defined initially. Phenyl-lower alkoxy-acetyl is especially benzyloxyacetyl or 2-phenylethoxyacetyl. Di-lower alkyl-amino-lower alkoxyacetyl is preferably 2-dimethyl-or 2-diethyl-aminoethoxyacetyl.

The invention relates especially to those compounds of the formula IV in which Ph and $R_1$ have the meanings defined for the particular preferred categories of compounds of the formula I and $X_1$ is lower alkoxy-acetyl, in particular having not more than 6 carbon atoms, such as methoxyacetyl or ethoxyacetyl, or, preferably, glycoloyl.

The compounds of the formula IV, which have been mentioned as starting materials, can be prepared by methods which are known per se, preferably by reacting a compound of the formula

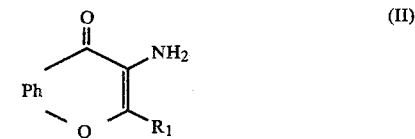

or an acid addition salt thereof, with an acid of the formula $X_1$—OH (IVa), or a functional derivative thereof.

Functional derivatives of acids of the formula IVa are, in particular, acid derivatives which contain an esterified or amidated carboxyl group or a carboxyl group in the form of an anhydride, such as lower alkoxy-carbonyl, substituted or unsubstituted carbamyl, for example carbamyl di-lower alkyl-carbamyl or imidazolyl-1-carbonyl, or halogenocarbonyl, for example chlorocarbonyl or bromocarbonyl. Examples of acids of the formula IVa and functional derivatives thereof are, in particular: for the preparation of compounds of the formula IV in which $X_1$ is a radical which can be solvolysed to a group R—C(=O)—, oxalyl halides, such as oxalyl chloride or oxalyl bromide, lower alkyl tri-lower alkoxy-acetates and lower alkyl dihalogeno-lower alkoxy-acetates, such as tetraethyl oxalate or diethyl dichlorooxalate, dialkyl imino-oxalates, such as diethyl monoimino-oxalate or diethyl diimino-oxalate, oxalic acid amidines, such as N-lower alkyl-oxalic acid ester-amidines, lower alkyl dithiooxalates, such as dimethyl dithio-oxalate, cyano-formyl chloride and cyanogen, and, for the preparation of compounds of the formula IV in which $X_1$ is a radical which can be oxidised to a group R—C—(=O)—, glycollic acid and its lower alkyl esters and the corresponding lactide, or mono- or di-lower alkoxyacetic acid and the lower alkyl esters thereof, for example ethyl ethoxyacetate or ethyl diethoxyacetate, halogenoacetic anhydrides, such as chloroacetic anhydride or chloroacetyl chloride, and tartaric acid, and also cinnamoyl chloride, acetyl chloride and glycine.

The reaction of compounds of the formula II with acids of the formula IVa and derivatives thereof can be carried out in a conventional manner, for example in the presence of a water-binding agent, such as an acid anhydride, for example phosphorus pentoxide, or dicyclohexylcarbodiimide, or of a condensing agent, for example an acid or basic condensing agent, such as a mineral acid, for example hydrochloric acid, or an alkali metal hydroxide or alkali metal carbonate, for example sodium hydroxide or potassium hydroxide, or of an organic nitrogen base, for example triethylamine or pyridine. In the case of the reaction with an acid anhydride, such as an acid chloride, an organic nitrogen base is preferably used as the condensing agent. The reaction with carboxylic acids is preferably carried out in the presence of a water-binding agent. If necessary, the reaction is in each case carried out in an inert solvent, at normal temperature or with cooling or warming, for example in the temperature range from about 0° C. to about 100° C., in a closed vessel and/or under an inert gas, for example nitrogen.

Compounds of the formula IV in which $X_1$ is glyoxyloyl can also be prepared by heating a corresponding halogenoacetyl compound, such as a bromoacetyl compound, with hexamethylenetetramine, preferably in an aqueous alcohol. Compounds of the formula IV in which $X_1$ is substituted or unsubstituted benzyliminoacetyl, can be prepared starting from the corresponding glycyl compounds by reacting these with substituted or unsubstituted benzaldehyde, and rearranging the benzylidene-glycyl compound thus obtainable, preferably under the reaction conditions.

Functionally modified oxalo groups containing an imino-ether grouping as the functionally modified carboxyl group can be prepared starting from the corresponding cyanocarbonyl compound by reaction with the corresponding alcohol, and cyclic imino-ethers can be prepared by treatment with a lower alkanediol or amino-lower alkanol.

Compounds of the formula IV, wherein $X_1$ denotes a glycoloyl radical which is optionally etherified or is esterified with a carboxylic acid, can also be manufactured by converting, in a compound of the formula

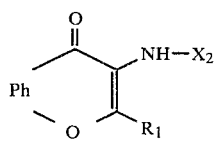

(IV'), wherein $X_2$ denotes a radical which can be converted into said group $X_1$, or in a salt thereof the group $X_2$ into a group $X_1$ and optionally converting a compound which can thus be obtained into another compound of the formula IV, wherein $X_1$ has the meaning indicated hereinbefore.

Groups $X_2$ are, for example, esterified glycoloyl groups different from glycoloyl esterified with a carboxylic acid, such as glycololyl esterified with a mineralic acid, such as chloroacetyl, bromoacetyl or iodoacetyl. These groups can be hydrolytically, for example in the presence of a basic hydrolysing agent, such as sodium hydroxide, converted into the glycoloyl group or can be, by reaction with a salt, such as the sodium salt of a corresponding alcohol or carboxylic acid be converted into etherified glycoloyl or glycoloyl esterified with a carboxylic acid.

Further groups $X_2$ which can be converted into group $X_1$ are, for example, radicals which can be converted into glycoloyl by reduction, such as the optionally hydrated glyoxyloyl group, which, under the reaction conditions, can also be formed by reduction of an oxalo group which may also be present in the form of a salt, anhydride or ester, or can be set free by hydrolysing a corresponding acetal, such as diethyl or ethylen acetal. As reducing agents there may be applied, for example, light-metal or dilight-metal hydrides, such as sodium-borohydride boron hydrides, for example, borane or diboran, or lithiumanilinoborohydride.

A compound of the formula I or IV which is obtainable according to the invention can be converted into another compound of the formula I or IV in a manner known per se.

Thus, for example, a free carboxyl group R can be esterified to an esterified carboxyl group R in a customary manner, for example by treatment with a diazo-lower alkane, which is unsubstituted or substituted by substituted or unsubstituted phenyl, or a tri-lower alkyl-oxonium, tri-lower alkyl-carboxonium or di-lower alkyl-carbonium salt, such as the hexachloroantimonate or hexafluorophosphate, or, in particular, by reaction with the corresponding alcohol or a reactive ester, such as a carboxylic acid ester, phosphorous acid ester, sulphurous acid ester or carbonic acid ester, for example a lower alkane-carboxylic acid ester, a tri-lower alkyl phosphite, di-lower alkyl sulphite or the carbonate or pyrocarbonate thereof, or a mineral acid ester or sulphonic acid ester, for example the hydrochloric acid ester or hydrobromic acid ester or sulphuric acid ester, benzenesulphonic acid ester, toluenesulphonic acid ester or methanesulphonic acid ester, of the corresponding alcohol, or with an olefin derived therefrom.

The reaction with the corresponding alcohol itself can advantageously be carried out in the presence of an acid catalyst, such as a proton acid, for example hydrochloric acid or hydrobromic acid, sulphuric acid, phosphoric acid, boric acid, benzenesulphonic acid and/or toluenesulphonic acid, or a Lewis acid, for example boron trifluoride-etherate, in an inert solvent, especially an excess of the alcohol employed, and, if necessary, in the presence of a water-binding agent and/or with removal of the water of reaction by distillation, for example as an azeotrope, and/or at elevated temperature.

The reaction with a reactive derivative of the corresponding alcohol can be carried out in a customary manner and, in the case of the reaction with a carboxylic acid ester, phosphorous acid ester, sulphurous acid ester or carbonic acid ester, can be carried out, for example, in the presence of an acid catalyst, such as one of those mentioned above, in an inert solvent, such as an aromatic hydrocarbon, for example in benzene or toluene, or in an excess of the alcohol derivative employed or of the corresponding alcohol, the water of reaction being distilled off if necessary, for example as an azeotrope. In the case of the reaction with a mineral acid ester or sulphonic acid ester, the acid to be esterified is advantageously employed in the form of a salt, for example the sodium or potassium salt, and the reaction is carried out, if necessary, in the presence of a basic condensing agent, such as an inorganic base, for example sodium hydroxide or sodium carbonate, potassium hydroxide or potassium carbonate or calcium hydroxide or calcium carbonate, or of a tertiary organic nitrogen base, for example triethylamine or pyridine, and/or in an inert solvent, such as one of the above tertiary nitrogen bases or a polar solvent, for example in dimethylformamide, and/or at elevated temperature.

The reaction with an olefin can be carried out, for example, in the presence of an acid catalyst, for example a Lewis acid, for example boron trifluoride, or a sulphonic acid, for example p-toluenesulphonic acid, or of a basic catalyst, for example sodium hydroxide or potassium hydroxide, advantageously in an inert solvent, such as an ether, for example in diethyl ether or tetrahydrofuran.

A free carboxyl group R can, furthermore, be converted into an amidated carboxyl group R by reaction with ammonia or an amine containing at least one hydrogen atom, in a customary manner, with dehydration of the ammonium salt formed as an intermediate, for example by azeotropic distillation with benzene or toluene or by dry heating.

The conversions, described above, of free carboxyl groups R into esterified or amidated carboxyl groups R can, however, also be carried out by first converting a compound of the formula (I), in which R is carboxyl, into a reactive derivative in a customary manner, for example into an acid halide by means of a halide of phosphorus or sulphur, for example by means of phosphorus trichloride or phosphorus tribromide, phosphorus pentachloride or thionyl chloride, or into a reactive ester, i.e. ester having electron-attracting structures, such as the ester with phenol, thiophenol, p-nitrophenol or cyanomethyl alcohol, by reaction with a corresponding alcohol, or into a reactive amide, for example the amide derived from imidazole or 3,5-dimethyl-pyrazole, by reaction with a corresponding amine. The resulting reactive derivative can then be reacted in a customary manner, for example as described below for the transesterification, transamidation and interconversion of esterified and amidated carboxyl groups R, with a corresponding alcohol, ammonia or the corresponding amine containing at least one hydrogen atom, to give the desired compound of the formula I.

An esterified carboxyl group R can be converted to the free carboxyl group R in customary manner, for example by hydrolysis in the presence of a catalyst, for example of a basic or acid agent, such as a strong base, for example sodium hydroxide or potassium hydroxide, or a mineral acid, for example hydrochloric acid, sulphuric acid or phosphoric acid, or to an amidated carboxyl group R, for example by reaction with ammonia or the corresponding amine containing at least one hydrogen atom.

An esterified carboxyl group R can also be transesterified to another esterified carboxyl group R in a customary manner, for example by reaction with a metal salt, such as the sodium or potassium salt, of a corresponding alcohol or with the alcohol itself, in the presence of a catalyst, for example of a strong base, for example sodium hydroxide or potassium hydroxide, or of a strong acid, such as a mineral acid, for example hydrochloric acid, sulphuric acid or phosphoric acid, or of an organic sulphonic acid, for example p-toluenesulphonic acid, or of a Lewis acid, for example boron trifluoride etherate.

An amidated carboxyl group R can be converted to the free carboxyl group R in a customary manner, for example by hydrolysis in the presence of a catalyst, for example of a strong base, such as an alkali metal hydroxyide or alkali metal carbonate or an alkaline earth metal hydroxide or alkaline earth metal carbonate, for example sodium hydroxide or sodium carbonate or potassium hydroxide or potassium carbonate, or of a strong acid, such as a mineral acid, for example hydrochloric acid, sulphuric acid or phosphoric acid.

Furthermore, on the radical Ph in a compound obtainable according to the invention, free, esterified or etherified hydroxyl groups can be converted into one another.

Thus, for example, a free hydroxyl group can be etherified to an etherified hydroxyl group, for example a lower alkoxy, hydroxy-lower alkoxy or lower alkylenedioxy group, by reaction with an etherifying agent, for example with a lower alkylating agent.

Etherifying agents are, for example, reactive esterified alcohols, such as lower alkanols or lower alkanediols esterified by a mineral acid, for example by hydriodic acid, hydrochloric acid or hydrobromic acid or sulphuric acid, or an organic sulphonic acid, for example by p-toluenesulphonic acid, p-bromobenzenesulphonic acid, benzenesulphonic acid, methanesulphonic acid, ethanesulphonic acid or ethenesulphonic acid, or fluorosulphonic acid, and also diazoalkanes. Etherifying agents are, in particular, lower alkyl chlorides, lower alkyl bromides or lower alkyl iodides, for example methyl iodide, lower alkylene halogenohydrins, for example ethylene chlorohydrin, di-lower alkyl sulphates, for example dimethyl sulphate or diethyl sulphate, or methyl fluorosulphonate, lower alkyl sulphonates, such as methyl p-toluenesulphonate, p-bromobenzenesulphonate, methanesulphonate or ethanesulphonate, epoxy-lower alkanes, for example propylene oxide, and also diazo-alkanes, for example diazomethane.

The reactions with etherifying agents, for example those singled out above, can be carried out in a customary manner, for example in an inert solvent, such as an ether, for example in tetrahydrofuran, in the case of the reaction with a diazoalkane or, when a reactive esterified alcohol is used, for example in the presence of a basic condensing agent, such as of an inorganic base, or example sodium hydroxide or sodium carbonate, potassium hydroxide or potassium carbonate or calcium hydroxide or calcium carbonate, or of a tertiary or quaternary nitrogen base, for example pyridine, triethylamine or tetraethyl-ammonium hydroxide or benzyltriethylammonium hydroxide, and/or of a solvent customary for the particular reaction, which solvent can also comprise an excess of the lower alkyl halide or lower alkyl sulphate used, for example, for the etherification, and/or a tertiary nitrogen base used as the basic condensing agent, for example triethylamine or pyridine, if necessary at elevated temperature. Methylation by means of methyl iodide in amyl alcohol/potassium carbonate at the boiling point is especially to be recommended.

Conversely, etherified hydroxyl can also be converted into hydroxyl in a customary manner, for example in the presence of an acid agent, such as a hydrogen halide acid, for example hydriodic acid, in an inert solvent, for example in ethanol or acetic acid.

In an analogous manner, esterified hydroxyl, such as halogen, can also be converted to etherified hydroxyl by reaction with a corresponding metal alcoholate, such as an alkali metal lower alkanolate, for example with sodium methanolate.

Furthermore, in a compound of the formula IV obtainable according to the invention, glycoloyl $X_1$ can be esterified by reaction with an esterifying agent, such as a lower alkanoic acid anhydride or acid chloride or benzoic acid anhydride or benzoyl chloride, or etherified by conversion to an alkali metal salt and reaction of the latter with a corresponding halogen compound, such as a lower alkyl halide. Conversely, esterified or etherified glycoloyl can be hydrolysed to glycoloyl, for example by acid catalysis.

Free compounds, obtainable according to the invention, of the formula I, in which R is carboxyl, can be converted into salts in a manner known per se, inter alia by treatment with a base or with a suitable salt of a carboxylic acid, usually in the presence of a solvent or diluent.

Salts obtainable according to the invention can be converted into the free compounds in a manner known per se, for example by treatment with an acid reagent, such as a mineral acid.

The compounds, including their salts, can also be obtained in the form of their hydrates or can incorporate the solvent used for crystallisation.

Because of the close relationship between the novel compounds in the free form and in the form of their salts, what is stated in this specification in respect of the free compounds or the salts thereof also applies by analogy to the corresponding salts and free compounds.

The invention also relates to those embodiments of the process in which a compound obtainable as an intermediate at any stage of the process is used as the starting material and the missing steps are carried out, or a starting material is used in the form of a salt and/or racemate or antipode or, especially, is formed under the reaction conditions.

Preferably, the starting materials used are in each case those which result in the object compounds designated initially as a preferred subject of the invention.

The present invention also relates to pharmaceutical preparations which contain compounds of the formula I or pharmaceutically usable salts thereof. The pharmaceutical preparations according to the invention are those which are intended for topical and local application and for enteral, such as oral or rectal, and parenteral administration to, and for inhalation by, warm-blooded animals and contain the pharmacological active ingredient on its own or together with a pharmaceutically usable carrier. The dosage of the active ingredient depends on the species of warm-blooded animal, the age and the individual condition, and also on the mode of administration.

The novel pharmaceutical preparations contain, for example, from about 10% to about 95%, and preferably from about 20% to about 90%, of the active ingredient. Pharmaceutical preparations according to the invention are, for example, those in the form of an aerosol or spray or in dosage unit forms, such as sugar-coated tablets, tablets, capsules or suppositories, and also ampoules.

The pharmaceutical preparations of the present invention are prepared in a manner known per se, for example by means of conventional mixing, granulating, sugar-coating, dissolving or lyophilising processes. Thus, pharmaceutical preparations for oral use can be obtained by combining the active ingredient with solid carriers, granulating or resulting mixture if desired and processing the mixture or granules, after adding suitable adjuncts if desired or necessary, to give tablets or sugar-coated tablet cores.

Suitable carriers are, especially, fillers, such as sugars, for example lactose, sucrose, mannitol or sorbitol, cellulose preparations and/or calcium phosphates, for example tricalcium phosphate or calcium hydrogen phosphate, as well as binders, such as starch pastes using, for example, maize starch, wheat starch, rice starch or potato starch, gelatin, tragacanth, methylcellulose and/or polyvinylpyrrolidone, and/or, if desired, disintegrators, such as the above starches, and also carboxymethyl-starch, crosslinked polyvinylpyrrolidone, agar or alginic acid or a salt thereof, such as sodium alginate. Adjuncts are, in particular, glidants and lubricants, for example silica, talc, stearic acid or salts thereof, such as magnesium stearate or calcium stearate, and/or polyethylene glycol. Sugar-coated tablet cores are provided with suitable coatings, which can be resistant to gastric juices, using, inter alia, concentrated sugar solutions which may contain gum arabic, talc, polyvinylpyrrolidone, polyethylene glycol and/or titanium dioxide, shellack solutions in suitable organic solvents or solvent mixtures or, for the preparation of coatings resistant to gastric juices, solutions of suitable cellulose preparations, such as acetylcellulose phthalate or hydroxypropylmethylcellulose phthalate. Dyes or pigments can be added to the tablets or the coatings of sugar-coated tablets, for example to identify or characterise different doses of the active ingredient.

Further pharmaceutical preparations for oral administration are dry-filled capsules made from gelatin, and also soft, sealed capsules made from gelatin and a plasticiser, such as glycerin or sorbitol. The dry-filled capsules can contain the active ingredient in the form of granules, for example mixed with fillers, such as lactose, binders, such as starches, and/or lubricants, such as talc or magnesium stearate, and can contain stabilisers. In soft capsules, the active ingredient is preferably dissolved or suspended in suitable liquids, such as fatty oils, liquid paraffin or liquid polyethylene glycols, to which stabilisers can also be added.

Pharmaceutical preparations for rectal administration are, for example, suppositories, which consist of a combination of the active ingredient with a suppository base. Suitable suppository bases are, for example, natural or synthetic triglycerides, paraffin hydrocarbons, polyethylene glycols or higher alkanols. Gelatin rectal capsules which contain a combination of the active ingredient with a base can also be used; base materials are, for example, liquid triglycerides, polyethylene glycols or paraffin hydrocarbons.

Preparations suitable for parenteral administration are, in particular, aqueous solutions of an active ingredient in the water-soluble form, for example of a water-soluble salt, and also suspensions of the active ingredient, such as corresponding oily injection suspensions, in which case suitable lipophilic solvents or vehicles, such as fatty oils, for example sesame oil, or synthetic fatty acid esters, for example ethyl oleate or triglycerides, are used, or aqueous injection suspensions which contain substances which increase the viscosity, for example sodium carboxymethylcellulose, sorbitol and/or dextran, and can also contain stabilisers.

Inhalation preparations for the treatment of the respiratory passages by nasal or buccal administration are, for example, aerosols or sprays which can disperse the pharmacological active ingredient in the form of a powder or in the form of drops of a solution or suspension. Preparations which have powder-dispersing properties usually contain, in addition to the active ingredient, a liquid propellant gas which has a boiling point below room temperature and also, if desired, carriers, such as liquid or solid non-ionic or anionic surfactants and/or solid diluents. Preparations in which the pharmacological active ingredient is in solution contain, in addition to this active ingredient, a suitable propellant and also, if necessary, an additional solvent and/or a stabiliser. In place of the propellant gas, it is also possible to use compressed air and this can be produced as required by means of a suitable compression and pressure release device.

Pharmaceutical preparations for topical and local use are, for example, lotions and creams which contain a liquid or semi-solid oil-in-water or water-in-oil emulsion, and ointments (such preparations preferably containing a preservative) for the treatment of the skin, eyedrops which contain the active ingredient in aqueous or oily solution and eye ointments, which are preferably prepared in a sterile form, for the treatment of the eyes, powders, aerosols and sprays (similar to those described above for the treatment of the respiratory passages) and also coarse powders, which are administered through the nostrils by rapid inhalation, and nose-drops, which contain the active compound in aqueous or oily solution, for the treatment of the nose, or lozenges, which contain the active compound in a composition generally consisting of sugar and gum arabic or tragacanth, to which flavourings can be added, as well as pastilles, which contain the active ingredient in an inert composition, for example consisting of gelatine and glycerin or sugar and gum arabic, for the local treatment of the mouth.

The invention also relates to the use of the novel compounds of the formula (I) and salts thereof, as pharmacologically active compounds and especially as anti-allergic agents, preferably in the form of pharmaceutical preparations. The daily dose which is administered to a warm-blooded animal weighing about 70 kg is from about 200 mg to about 1,200 mg.

The following Examples illustrate the present invention without in any way restricting the scope thereof. Temperatures are in degrees centigrade.

EXAMPLE 1

4.5 g of monomethyl oxalate chloride are added dropwise, in an anhydrous atmosphere, at 10°, to a solution of 3.7 g of triethylamine and 5 g of 3-amino-4-oxo-4H-1-benzopyrane in 100 ml of chloroform, with stirring. After the addition has ended, the mixture is stirred for a further 90 minutes at room temperature. The reaction solution is then partitioned between 3 times 50 ml of chloroform and 50 ml of 2 N hydrochloric acid. The organic phases are washed until neutral, dried over sodium sulphate and concentrated in vacuo. After adding ether to the concentrated solution, 3-methoxyoxalylamino-4-oxo-4H-1-benzopyrane with a melting point of 200°–201° crystallises out.

EXAMPLE 2

35 ml of N sodium hydroxide solution and then 1.3 l of water are added to a suspension of 7.6 g of 3-methoxyoxalylamino-4-oxo-4H-1-benzopyrane in 200 ml of ethanol. The mixture is now warmed at 70° for 15 minutes, with stirring. The pH of the solution, which is now clear, is adjusted to 2 with concentrated hydrochloric acid and the solution is slowly cooled to room temperature. On cooling, 3-oxaloamino-4-oxo-4H-1-benzopyrane with a melting point of 200° (decomposition) crystallises out.

EXAMPLE 3

The following compounds can also be prepared in a manner analogous to that described in Example 1 or 2: 6-hydroxy-3-methoxyoxalylamino-4-oxo-4H-1-benzopyrane, 6-hydroxy-3-oxaloamino-4-oxo-4H-1-benzopyrane, 6-chloro-3-methoxyoxalylamino-4-oxo-4H-1-benzopyrane, 6-chloro-3-oxaloamino-4-oxo-4H-1-benzopyrane, melting point 213°–215°, 6-methoxy-3-methoxyoxalylamino-4-oxo-4H-1-benzopyrane, melting point 174°–175°, 6-methoxy-3-oxaloamino-4-oxo-4H-1-benzopyrane, melting point 230°, 5,8-dimethyl-3-methoxyoxalylamino-4-oxo-4H-1-benzopyrane, 5,8-dimethyl-3-oxaloamino-4-oxo-4H-1-benzopyrane, 3-methoxyoxalylamino-6,7-trimethylene-4-oxo-4H-1-benzopyrane, melting point 185°–186°, and 3-oxaloamino-6,7-trimethylene-4-oxo-4H-1-benzopyrane, melting point 185°.

EXAMPLE 4

5,7-Dimethyl-3-methoxyoxalylamino-4-oxo-4H-1-benzopyrane with a melting point of 186°–187° (from ethanol) can be prepared in a manner analogous to that described in Example 1, using 3-amino-5,7-dimethyl-4-oxo-4H-1-benzopyrane as the starting material. The starting material can be obtained, for example, using 5,7-dimethyl-4-hydroxy-coumarin as the starting material, by reacting the latter with nitric acid in acetic acid at 80° to give 5,7-dimethyl-4-hydroxy-3-nitro-coumarin, treating this compound for 24 hours with sodium hydroxide solution and subsequently acidifying, with decarboxylation, to give 4,6-dimethyl-2-hydroxy-β-nitro-acetophenone, analogously to the process described in J. Am. Chem. Soc. 67, 99 (1945), and also reacting the latter compound with the mixed anhydride of formic acid and acetic acid to give 5,7-dimethyl-3-nitro-4-oxo-4H-1-benzopyrane with a melting point of 120°–125° and reducing this compound with sodium dithionite to give 3-amino-5,7-dimethyl-4-oxo-4H-1-benzopyrane (melting point 120°–121°), analogously to the process described in Tetrahedron Letters 1976, 719, and purifying this product via the hydrochloride.

EXAMPLE 5

Analogously to the process described in Example 4, 3-methoxyoxalylamino-8-methyl-4-oxo-4H-1-benzopyrane with a melting point of 164.5° is obtained using 4-hydroxy-8-methyl-coumarin as the starting material, via 4-hydroxy-8-methyl-3-nitro-coumarin with a melting point of 178°–180° (decomposition), 2-hydroxy-3-methyl-β-nitro-acetophenone with a melting point of 126°–128° (from ethanol), 8-methyl-3-nitro-4-oxo-4H-1-benzopyrane with a melting point of 85°–95° and 3-amino-8-methyl-4-oxo-4H-1-benzopyrane with a melting point of 151°–152°.

EXAMPLE 6

In a manner analogous to that described in Example 4, 6-methoxy-3-methoxyoxalylamino-4-oxo-4H-1-benzopyrane with a melting point of 174°–175° (from ethanol/chloroform) is obtained using 4-hydroxy-6-methoxy-coumarin as the starting material, via 4-hydroxy-6-methoxy-3-nitro-coumarin with a melting point of 172°–174°, 2-hydroxy-5-methoxy-β-nitro-acetophenone with a melting point of 143°–144° (from methylene chloride/petroleum ether), 6-methoxy-3-nitro-4-oxo-4H-1-benzopyrane with a melting point of 149°–150° and 3-amino-6-methoxy-4-oxo-4H-1-benzopyrane.

EXAMPLE 7

In a manner analogous to that described in Example 4, 6,7-dimethyl-3-methoxyoxalylamino-4-oxo-4H-1-benzopyrane with a melting point of 222°–224° (from chloroform/ethanol) is obtained using 6,7-dimethyl-4-hydroxy-coumarin as the starting material, via 6,7-dimethyl-4-hydroxy-3-nitro-coumarin with a melting point of 205°–207° (decomposition), 4,5-dimethyl-2-hydroxy-β-nitro-acetophenone with a melting point of 142°–144° (from methylene chloride/petroleum ether), 6,7-dimethyl-3-nitro-4-oxo-4H-1-benzopyrane with a melting point of 155°–157° and 3-amino-6,7-dimethyl-4-oxo-4H-1-benzopyrane with a melting point of 150°–152° (from chloroform/toluene).

EXAMPLE 8

In a manner analogous to that described in Example 4, 3-methoxyoxalylamino-6-methyl-4-oxo-4H-1-benzopyrane with a melting pont of 179.5° (from chloroform/ethanol) is obtained using 4-hydroxy-6-methyl-coumarin as the starting material, via 4-hydroxy-6-methyl-3-nitro-coumarin with a melting point of 178° (decomposition), 2-hydroxy-5-methyl-β-nitro-acetophenone with a melting point of 137°–138° (from ethanol), 6-methyl-3-nitro-4-oxo-4H-1-benzopyrane with a melting point of 97°–99° and 3-amino-6-methyl-4-oxo-4H-1-benzopyrane with a melting point of 96°–98° (from ethyl acetate/petroleum ether).

EXAMPLE 9

In a manner analogous to that described in Example 4, 3-methoxyoxalylamino-4-oxo-4,6,7,8-tetrahydrocyclopenta[g]-1-benzopyrane of the formula

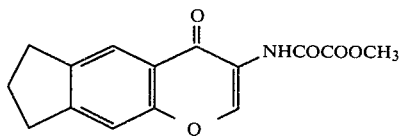

with a melting point of 185°–186° is obtained using 4-hydroxy-4,6,7,8-tetrahydro-2-oxo-cyclopenta[g]-1-benzopyrane as the starting material, via 4-hydroxy-3-nitro-4,6,7,8-tetrahydro-coumarin with a melting point of 215°–217° (decomposition), 5-(2-nitroacetyl)-6-hydroxyindane with a melting point of 115°–117° (from methylene chloride/petroleum ether), 3-nitro-4-oxo-4,6,7,8-tetrahydro-cyclopenta[g]-1-benzopyrane with a melting point of 145° (decomposition) and 3-amino-4-oxo-4,6,7,8-tetrahydrocyclopenta[g]-1-benzopyrane with a melting point of 151°–152° (from ethyl acetate/petroleum ether).

EXAMPLE 10

The following compounds are obtained in a manner analogous to that described in Example 2: 5,7-dimethyl-3-oxaloamino-4-oxo-4H-1-benzopyrane with a melting point of 224° (decomposition, from water/ethanol), using 5,7-dimethyl-3-methoxyoxalylamino-4-oxo-4H-1-benzopyrane as the starting material, 6,7-dimethyl-3-oxaloamino-4-oxo-4H-1-benzopyrane with a melting point of 205° (from water/ethanol), using 6,7-dimethyl-3-methoxyoxalylamino-4-oxo-4H-1-benzopyrane as the starting material, 6-methoxy-3-oxaloamino-4-oxo-4H-1-benzopyrane with a melting point of 230° (from water/ethanol), using 6-methoxy-3-methoxy-oxalylamino-4-oxo-4H-1-benzopyrane as the starting material, 6-methyl-3-oxaloamino-4-oxo-4H-1-benzopyrane with a melting point of 199.5° (from water/ethanol), using 3-methoxyoxalylamino-6-methyl-4-oxo-4H-1-benzopyrane as the starting material and 3-oxaloamino-4-oxo-4,6,7,8-tetrahydro-cyclopenta[g]-1-benzopyrane with a melting point of 185° (decomposition), using 3-methoxyoxalylamino-4-oxo-4,6,7,8-tetrahydro-cyclopenta[g]-1-benzopyrane as the starting material.

EXAMPLE 11

A suspension of 9 g of 3-amino-4-oxo-4H-1-benzopyrane in 3.6 g of dimethyl oxalate and 300 ml of xylene is heated to the boil, with cooling, in a nitrogen atmosphere. About 200 ml of xylene are distilled off in the course of 24 hours. The mixture is now allowed to cool to 90° and the precipitate formed, which consists of a by-product, is filtered off and the filtrate is evaporated to dryness. 3-Methoxyoxalylamino-4-oxo-4H-1-benzopyrane with a melting point of 200°–201° is obtained from the evaporation residue, from ethanol/petroleum ether.

EXAMPLE 12

The following compounds are also obtained in a manner analogous to that described in Examples 1 to 11: 6-chloro-3-methoxyoxalylamino-7-methyl-4-oxo-4H-1-benzopyrane, 6-chloro-7-methyl-3-oxaloamino-4-oxo-4H-1-benzopyrane, 6-chloro-3-methoxyoxalylamino-8-methyl-4-oxo-4H-1-benzopyrane and 6-chloro-8-methyl-3-oxaloamino-1-benzopyrane.

EXAMPLE 13

Tablets containing 0.1 g of 5,7-dimethyl-3-methoxyoxalylamino-4-oxo-4H-1-benzopyrane are prepared as follows:

| Composition (for 1,000 tablets): | |
| --- | --- |
| 5,7-Dimethyl-3-Methoxyoxalylamino-4-oxo-4H-1-benzopyrane | 100 g |
| Lactose | 50 g |
| Wheat starch | 73 g |
| Colloidal silica | 13 g |
| Magnesium stearate | 2 g |
| Talc | 12 g |
| Water | q.s. |

The 3-methoxyoxalylamino 4-oxo-4H-1-benzopyrane is mixed with a portion of the wheat starch and with the lactose and the colloidal silica, and the mixture is forced through a sieve. A further portion of the wheat starch is mixed to a paste with five times the amount of water on a waterbath and the above powder mixture is kneaded with this paste until a slightly plastic mass has formed. The plastic mass is pressed through a sieve of about 3 mm mesh width and dried and the dry granules are again forced through a sieve. The remainder of the wheat starch, the talc and the magnesium stearate are then mixed in and the resulting mixture is compressed to tablets weighing 0.25 g.

Tablets each containing 0.1 g of 5,8-dimethyl-3-methoxyoxalylamino-4-oxo-4H-1-benzopyrane, 5,7- or 5,8-dimethyl-3-oxaloamino-4-oxo-4H-1-benzopyrane, 3-methoxyoxalylamino-6,7-trimethylene-4-oxo-4H-1-benzopyrane or 3-oxaloamino-6,7-trimethylene-4-oxo-4H-1-benzopyrane can also be prepared in an analogous manner.

EXAMPLE 14

An approximately 2% aqueous solution, suitable for inhalation, of a water-soluble active ingredient according to the invention, in the free form or in the form of the sodium salt, can be prepared, for example, in the following composition:

| Composition | |
|---|---|
| Active ingredient, for example 5,7-dimethyl-3-oxaloamino-4-oxo-4H-1-benzopyrane | 2,000 mg |
| Stabiliser, for example disodium ethylenediaminetetraacetate | 10 mg |
| Preservative, for example benzalkonium chloride | 10 mg |
| Freshly distilled water | to make up to 100 ml |

PREPARATION

The active ingredient is dissolved in freshly distilled water with the addition of the equimolecular amount of 2 N sodium hydroxide solution. The stabiliser and the preservative are then added. After all the components have dissolved completely, the resulting solution is made up to 100 ml and filled into small bottles and these are sealed gas-tight.

2% aqueous inhalation solutions containing 5,7- or 5,8-dimethyl-3-methoxyoxalylamino-4-oxo-4H-1-benzopyrane, 5,8-dimethyl-3-oxaloamino-4-oxo-4H-1-benzopyrane, 3-methoxyoxalylamino-6,7-trimethylene-4-oxo-4H-1-benzopyrane or 3-oxaloamino-6,7-trimethylene-4-oxo-4H-1-benzopyrane can also be prepared in an analogous manner.

EXAMPLE 15

Capsules, suitable for insufflation, containing about 25 mg of an active ingredient according to the invention, can be prepared, for example, as follows:

| Composition | |
|---|---|
| Active ingredient, for example 5,7-dimethyl-3-methoxy-oxyalylamino-4-oxo-4H-1-benzopyrane | 25 mg |
| Very finely ground lactose | 25 mg |

PREPARATION

The active ingredient and the lactose are intimately mixed. The resulting powder is then sieved and filled in 50 mg portions into 1,000 gelatin capsules.

Insufflation capsules containing 25 mg of 5,8-dimethyl-3-methoxyoxalylamino-4-oxo-4H-1-benzopyrane, 5,7- or 5,8-dimethyl-3-oxaloamino-4-oxo-4H-1-benzopyrane, 3-methoxyoxalylamino-6,7-trimethylene-4-oxo-4H-1-benzopyrane or 3-oxaloamino-6,7-trimethylene-4-oxo-4H-1-benzopyrane can also be prepared in an analogous manner.

EXAMPLE 16

Pharmaceutical preparations containing N-(6,7-dimethyl-4-oxo-4H-benzopyran-3-yl)-oxamide, 6,7-dimethyl-3-methoxy-oxalylamino-4-oxo-4H-1-benzopyrane, 6,7-dimethyl-3-oxaloamino-4-oxo-4H-1-benzopyrane, 3-methoxyoxalylamino-4-oxo-2,6,7-trimethyl-4H-1-benzopyrane, 3-oxaloamino-4-oxo-2,6,7-trimethyl-4H-1-benzopyrane, 3-glycoloylamino-4-oxo-4,6,7,8-tetrahydro-cyclopenta[g]-1-benzopyrane or 3-acetoxyglycoloylamino-4-oxo-4,6,7,8-tetrahydro-cyclopenta[g]-1-benzopyrane as the active ingredient can be prepared in a manner analogous to that described in Examples 20-22.

EXAMPLE 17

15 ml of saturated methanolic ammonia solution are added to a solution of 0.2 g of 6,7-dimethyl-3-methoxyoxalylamino-4-oxo-4H-1-benzopyrane in 30 ml of methanol and 20 ml of methylene chloride. The N-(6,7-dimethyl-4-oxo-4H-1-benzopyran-3-yl)-oxamide which precipitates is filtered off, washed with a little methanol and dried; it melts at 280°–282°.

EXAMPLE 18

0.5 g of 3-chloro-oxalylamino-5,7-dimethyl-4-oxo-4H-1-benzopyrane are added to a mixture, which has been warmed to 60°, of 50 ml of ethanol and 0.5 ml of 2 N sodium hydroxide solution. 300 ml of water are added and the resulting mixture is warmed to 60° and then acidified to pH=1 with 2 N hydrochloric acid. The precipitate which separates out is filtered off, washed with a little ethanol and dried. This yields 5,7-dimethyl-3-oxaloamino-4-oxo-1-benzopyrane with a melting point of 222° (decomposition).

The starting material can be prepared as follows:

A solution of 0.5 g of 3-amino-5,7-dimethyl-4-oxo-4H-1-benzopyrane in 5 ml of chloroform is added slowly dropwise to 5 ml of oxalyl chloride, under nitrogen. The mixture is stirred for a further one hour and evaporated to dryness under reduced pressure, the evaporation residue is dissolved in 30 ml of chloroform, the solution is filtered and the filtrate is again evaporated to dryness. This yields 3-chloro-oxalylamino-5,7-dimethyl-4-oxo-4H-1-benzopyrane with a melting point of 150°–153°.

EXAMPLE 19

0.2 g of potassium permanganate is added to a solution of 0.2 g of 3-glycoloylamino-4-oxo-4,6,7,8-tetrahydro-cyclopenta[g]-1-benzopyrane in 40 ml of acetone and 40 ml of water and the mixture is stirred for 40 hours at room temperature. The precipitate which has formed is filtered off, the filtrate is acidified with 2 N hydrochloric acid and the precipitate which separates out is filtered off. This yields 3-oxaloamino-4-oxo-4,6,7,8-tetrahydro-cyclopenta[g]-1-benzopyrane with a melting point of 185° (decomposition).

The starting material can be prepared, for example, as follows:

7 g of glycollic acid are added to 6 g of 3-amino-4-oxo-4,6,7,8-tetrahydro-cyclopenta[g]-1-benzopyrane. The reaction mixture is warmed at 120° for 1 hour. It is allowed to cool to room temperature and is digested with water and filtered and the material on the filter is dried and recrystallised from 400 ml of ethanol and then from a little ethyl acetate. This yields 3-glycoloylamino-4-oxo-4,6,7,8-tetrahydro-cyclopenta[g]-1-benzopyrane with a melting point of 199°–200°.

3-Acetoxyglycoloylamino-4-oxo-4,6,7,8-tetrahydrocyclopenta[g]-1-benzopyrane with a melting point of 199°–200° can be prepared from the latter by conventional acetylation with acetic anhydride.

EXAMPLE 20

In a manner analogous to that described in Example 1, reaction of 3-amino-4-oxo-2,6,7-trimethyl-4H-1-benzopyrane with methyl oxalate chloride yields 3-methoxy-oxalylamino-4-oxo-2,6,7-trimethyl-4H-1-benzopyrane with a melting point of 210°–211°. The starting material can be prepared in a conventional manner, using 6,7-dimethyl-4-hydroxy-3-nitro-coumarin as the starting material, by treatment with sodium hydroxide solution and acid decarboxylation to give 2-hydroxy-4,5-dimethyl-β-nitro-acetophenone, reaction of the latter with formic anhydride in the presence of acetic anhydride to give 3-nitro-4-oxo-2,6,7-trimethyl-4H-1-benzopyrane with a melting point of 175°–177° and hydrogenation of this compound in the presence of palladium-on-calcium carbonate in dimethylformamide.

EXAMPLE 21

In a manner analogous to that described in Example 2, 3-oxaloamino-4-oxo-2,6,7-trimethyl-4H-1-benzopyrane with a melting point above 200° (decomposition) is obtained using 3-methoxyoxalylamino-4-oxo-2,6,7-trimethyl-4H-1-benzopyrane as the starting material.

What is claimed is:

1. A 3-oxaloamino-4-oxo-4H-1-benzopyrane derivative of the formula I

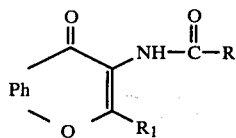

(I)

in which R is carboxyl, lower alkoxycarbonyl or carbamyl which is unsubstituted or mono- or di-sub-stituted by lower alkyl, Ph is 1,2-phenylene which is di-substituted by lower alkyl, or, at two adjacent carbon atoms, by 3-membered or 4-membered lower alkylene, and $R_1$ is hydrogen or lower alkyl, in the free form or in the form of a salt.

2. A compound according to claim 1, in which R is carboxyl, Ph is 1,2-phenylene which is di-substituted by lower alkyl having not more than 4 C atoms, or, on two adjacent C atoms, by lower alkylene having not more than 4 C atoms, and $R_1$ is hydrogen, in the free form or in the form of a salt.

3. A compound according to claim 1, of the formula Ia

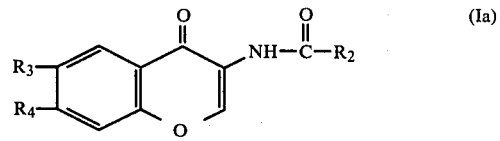

(Ia)

in which $R_2$ is carboxyl and $R_3$ and $R_4$ independently of one another are lower alkyl having not more than 4 C atoms, or together are a 3-membered or 4-membered lower alkylene radical having not more than 4 C atoms, in the free form or in the form of a pharmaceutically usable salt.

4. A compound as claimed in claim 1 being 3-oxaloamino-6,7-trimethylene-4-oxo-4H-1-benzopyrane or a pharmaceutically usable salt thereof.

5. A compound as claimed in claim 1 being 5,7-dimethyl-3-methoxyoxalylamino-4-oxo-4H-1-benzopyrane.

6. A compound as claimed in claim 1 being 5,7-dimethyl-3-oxaloamino-4-oxo-4H-1-benzopyrane or a pharmaceutically usable salt thereof.

7. A compound as claimed in claim 1 being 6,7-dimethyl-3-oxaloamino-4-oxo-4H-1-benzopyrane or a pharmaceutically usable salt thereof.

8. An antiallergic pharmaceutical preparation containing an antiallergically effective amount of a compound claimed in claim 1 or a pharmaceutically usable salt thereof together with conventional pharmaceutical carriers andl/or auxilliaries.

* * * * *